United States Patent
Grunlan et al.

(10) Patent No.: US 9,925,297 B2
(45) Date of Patent: Mar. 27, 2018

(54) SHAPE MEMORY POLYMER SCAFFOLDS FOR TISSUE DEFECTS

(71) Applicant: The Texas A&M University System, College Station, TX (US)

(72) Inventors: Melissa A. Grunlan, College Station, TX (US); Dawei Zhang, Beijing (CN); Cody A. Schoener, Midland, MI (US); William B. Saunders, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/218,043

(22) Filed: Jul. 24, 2016

(65) Prior Publication Data

US 2017/0021060 A1    Jan. 26, 2017

Related U.S. Application Data

(60) Provisional application No. 62/196,723, filed on Jul. 24, 2015.

(51) Int. Cl.
| | |
|---|---|
| *A61L 27/16* | (2006.01) |
| *A61L 27/18* | (2006.01) |
| *A61L 27/56* | (2006.01) |
| *A61L 27/44* | (2006.01) |
| *B29C 35/08* | (2006.01) |
| *B29L 31/00* | (2006.01) |

(52) U.S. Cl.
CPC ............ *A61L 27/18* (2013.01); *A61L 27/446* (2013.01); *A61L 27/56* (2013.01); *A61L 2400/08* (2013.01); *A61L 2400/16* (2013.01); *A61L 2430/02* (2013.01); *B29C 2035/0827* (2013.01); *B29K 2995/0056* (2013.01); *B29L 2031/7532* (2013.01)

(58) Field of Classification Search
CPC ........ C08L 67/04; A61L 27/18; A61L 27/446; A61L 2400/08; A61L 2400/16; A61L 2430/02; A61L 27/56; B29C 2035/0827; B29K 2995/0056; B29L 2031/7532
See application file for complete search history.

(56) References Cited

PUBLICATIONS

Zhang et al. (Polymer 2012;53:2935-2941).*
Kweon et al. (Biomaterials 2003;24:801-808).*
Schoener et al. (Journal of Materials Chemistry 2010;20:1787-1788; 2 pages).*
Woodard et al. (Biomacromolecules 2017; 18: 4075-4083.) (Year: 2017).*
Woodard et al. (Macromolecular Rapid Communications Oct. 2016; 37: 1972-1977.) (Year: 2016).*
Wang et al. (Journal of Applied Polymer Science. 2007;104:4182-4187.) (Year: 2007).*
Nagata e t al. (Macromol. Chem. Phys. 2010;211:1826-1835.) (Year: 2010).*
Zhang et al, "A Bioactive 'Self-Fitting' Shape Memory Polymer Scaffold with Potential to Treat Cranio-Maxillo Facial Bone Defects", Acta Biomaterialia, 10, pp. 4597-4605, 2014.

* cited by examiner

*Primary Examiner* — Ernst V Arnold
(74) *Attorney, Agent, or Firm* — Winstead PC (57) ABSTRACT

A method of making a shape memory polymer (SMP) tissue scaffold includes forming a salt template and adding a macromer solution to the salt template. The macromer solution may include a photoinitiator solution. The method includes drying the SMP scaffold and leaching salt from the SMP scaffold. A coating is then applied to the SMP scaffold. The coating may be applied either before or after heating the SMP scaffold.

15 Claims, 1 Drawing Sheet

SHAPE MEMORY POLYMER SCAFFOLDS FOR TISSUE DEFECTS

CROSS-REFERENCE TO RELATED APPLICATIONS

This application claims priority to U.S. Provisional Application Ser. No. 62/196,723 filed Jul. 24, 2016, which is incorporated herein by reference in its entirety.

STATEMENT REGARDING FEDERALLY SPONSORED RESEARCH OR DEVELOPMENT

This invention was made with government support under Contract No. R01EB000462 awarded by The National Institutes of Health/National Institute of Biomedical Imaging and Bioengineering. The government has certain rights in the invention.

TECHNICAL FIELD

The present disclosure relates to tissue scaffolds. In particular, it relates to conformable shape memory polymer (SMP) tissue scaffolds.

BACKGROUND

Bone, cartilage, joint, and other defects may form in tissue due to events such as malformation, injury, disease, tissue removal, and surgeries. Biological and synthetic tissue grafts have been used to repair these tissue defects. Biological tissue grafts such as autografts may use tissue from another site of the body to fit to and repair the tissue defect. However, suitable autograft sites are limited and the procedure is complex. The autograft must be shaped and fixed to the defect so as to significantly contact the surrounding tissue. Poor contact between the autograft and the tissue may increase the risk of graft adsorption. Synthetic tissue grafts, such as putties and cements, may conformally fit to the surface, but are not bioactive and may fracture. Critical-sized cranio-maxillofacial (CMF) bone defects and other tissue defects require the use of biologic or synthetic bone grafts for functional support to guide the formation of new bone. The "gold standard" remains autografts, most often harvested from a patient's fibula, iliac crest, skull or mandible. However, autografts are associated with limited availability, donor site morbidity and complex grafting procedures. In particular, shaping and fixing the rigid autograft so as to tightly fit into the defect is difficult. An ill-fitting interface caused by poor contact between the graft and surrounding bone tissue increases the risk of graft resorption.

Precisely shaping the three-dimensional scaffold geometry so as to match the contours of an irregular bone defect is generally limited to mold shape, post-fabrication shaping and complex computer-aided solid free-form fabrication techniques. As a result, scaffolds based on in situ forming (e.g. injectable) materials have been explored. Many are hydrogels, but these lack mechanical strength and often exhibit variable local curing times leading to poor adhesion to the defect edges. In addition, the cytotoxicity of reagents (e.g. monomers, macromers, crosslinkers and catalysts) of some hydrogel systems may be problematic. Moreover, typical in situ forming hydrogels lack adequate pore size and interconnectivity and control thereof, which limits cellular migration and the rate of hydrogel biodegradation. In situ forming bioactive ceramics or glass-ceramics prepared with or without polymer matrices (e.g. bone putties) are limited by their brittle mechanical properties as well as low pore interconnectivity.

SUMMARY

A SMP scaffold was developed exhibiting an open porous structure and the capacity to conformally "self-fit" into irregular defects. The SMP scaffold was prepared via photocrosslinking of poly($\in$-caprolactone) diacrylate (PCL-DA) using a solvent casting/particulate leaching (SCPL) method, which included a fused salt template. A bioactive polydopamine coating was applied to coat the pore walls. Following exposure to warm saline at $T > T_{trans}$ ($T_{trans} = T_m$ of PCL), the scaffold became malleable and could be pressed into an irregular model defect. Cooling caused the scaffold to lock in its temporary shape within the defect. The polydopamine coating did not alter the physical properties of the scaffold. However, polydopamine-coated scaffolds exhibited superior bioactivity (i.e. formation of hydroxyapatite in vitro), osteoblast adhesion, proliferation, osteogenic gene expression and extracellular matrix deposition.

Tissue engineering has emerged as a treatment for CMF bone defects. Several properties of the biomaterial scaffold are critical to the success of this approach. First, the scaffold must form close contact with adjacent bone tissue to permit osseointegration. Second, the scaffold should be osteoconductive (i.e. permitting cell migration and neotissue infiltration). Finally, the scaffold should be bioactive (i.e. promoting integration/bonding with surrounding bone tissue and the attachment and differentiation of osteogenic cells).

A method of making a SMP tissue scaffold includes forming a salt template and adding a macromer solution to the salt template. The macromer solution may include a photoinitiator solution. The method includes drying the SMP scaffold and leaching salt from the SMP scaffold. A coating is then applied to the SMP scaffold. The coating may be applied either before or after heating the SMP scaffold.

A method for creating a SMP tissue scaffold includes creating a salt template from salt having a salt size and a degree of salt fusion. A macromer solution is then added to the salt template. The macromer solution is then polymerized to form a biocompatible SMP foam. The salt size, the macromer solution, and the degree of salt fusion are selected according to SMP foam pore size, pore morphology, modulus, and shape memory behavior suitable for tissue scaffold applications.

A SMP tissue scaffold includes a biocompatible SMP foam that includes a biostable segment, a filler, a biological treatment, and a coating. The biocompatible SMP foam has a transition temperature, pore size, pore morphology, modulus, and shape memory behavior suitable for tissue scaffold applications.

BRIEF DESCRIPTION OF THE DRAWINGS

The drawings included in the present application are incorporated into, and form a part of, the specification. They illustrate embodiments of the present invention and, along with the description, serve to explain the principles of the invention. The drawings are only illustrative of embodiments of the invention and do not limit the invention.

DETAILED DESCRIPTION

A thermoresponsive SMP scaffold was designed to "self-fit" into irregular bone defects, such as, for example, CMF bone defects. Thermoresponsive SMPs are a class of stimuli-sensitive materials whose shapes can be changed upon exposure to heat. The "netpoints" are chemical or physical crosslinks that define the permanent shape, while the "switching segments" maintain the temporary shape and recover the permanent shape when cycled through their thermal transition temperature ($T_{trans}$). $T_{trans}$ may be a glass transition temperature ($T_g$) or a melting transition temperature ($T_m$). Thus, an SMP may be sequentially deformed into a temporary shape at $T>T_{trans}$, fixed by cooling to $T<T_{trans}$ and the permanent shape recovered by heating again to $T>T_{trans}$. Solid, non-porous SMP have been explored for a variety of medical devices, including self-expanding cardiovascular stents and orthopedic fixation devices. Similarly, porous SMP have been investigated as embolic sponges for treating aneurysms and have recently been proposed for the repair of bone defects.

Poly($\in$-caprolactone) (PCL)-based SMPs have attracted much attention because of the biocompatibility, biodegradability, and elasticity of PCL. In addition, PCL has been extensively evaluated as a scaffold material for bone tissue engineering. For SMP applications, the $T_m$ of PCL serves as the $T_{trans}$, which may be conveniently tailored from 43 to 60° C. with increased PCL number average molecular weight ($M_n$). Porous SMP foams based on diacrylated (AcO) macromers containing PCL segments as well as optional polydimethylsiloxane (PDMS) segments (AcO-PCL$_{40}$-block-PDMS$_m$-block-PCL$_{40}$-OAc; m=0-130) have been fabricated using a revised solvent casting/particulate leaching (SCPL) method, which included photocrosslinking and salt fusion. By tailoring the fabrication variables such as salt particle size, degree of salt fusion and macromer concentration, SMP foams displaying excellent shape fixity ($R_f$) as well as highly tunable pore size, pore interconnectivity, modulus and percentage shape recovery ($R_r$) were prepared.

A bioactive self-fitting SMP scaffold was prepared based on PCL diacrylate (PCL-DA) ($M_n \approx 10,000$ g mol$^{-1}$) using the previously described SCPL method. The self-fitting property of the SMP scaffold originates from the PCL crystalline domains (i.e. switching segments), which, upon melting at $T>T_m$ (~55° C.), causes the scaffold to soften and become malleable. In this way, the scaffold is able to be manually compressed and pressed into an irregular model defect. Conformal "fitting" is achieved with the subsequent release of manual pressure, whereby shape recovery (i.e., expansion) of the scaffold continues until irregular boundaries are met. Upon cooling ($T<T_m$), recrystallization of PCL domains causes the scaffold to return to its relatively rigid state, thereby fixing the temporary shape and locking the scaffold in place within the defect. Pore interconnectivity as well as shape memory behavior were achieved using specific fabrication parameters previously identified. When inserted into a bone defect in vivo, bonding of the scaffold to adjacent bone tissue is critical. To promote bonding, a bioactive polydopamine coating was applied onto pore walls of the PCL SMP scaffold. Dopamine has been shown to form a thin layer of polydopamine that adheres to a wide variety of substrates. Under slightly basic conditions (pH=8.5), a coating of dopamine forms as a result of oxidative polymerization or possibly an aggregation process. Polydopamine-coated materials exhibit enhanced hydrophilicity and bioactivity in terms of their ability to form hydroxyapatite (HAp). In addition, in vivo testing has demonstrated that polydopamine coatings are biocompatible. In this study, pore features, surface hydrophilicity, as well as thermal, mechanical, and shape memory properties of the SMP scaffold before and after application of the polydopamine coating, were evaluated. To examine the ability to support bone regeneration, bioactivity as well as osteoblast adhesion, spreading, proliferation and gene expression were evaluated for polydopamine coated and uncoated SMP scaffolds.

According to embodiments of the disclosure, a SMP scaffold may be used to repair a tissue defect. These SMP scaffolds may form close contact with adjacent tissues due to the elasticity of the SMP. The SMP may have a soft state that is conducive to fitting or molding the scaffold into a tissue defect. Upon cooling, the SMP may transition to a rigid state that secures the scaffold into the tissue defect. The ability of the scaffold to conformally fit into the defect or augment existing tissue permits the necessary contact needed for integration and healing. Pore size, degradation rate, mechanical properties, surface properties, and other properties of the scaffold may be configured for the nature and environment of the tissue defect. The scaffold may be modified by external additives and processes such as fillers, coatings, and surface treatments.

According to embodiments of the disclosure, the SMP scaffold may be composed of a SMP formed from a variety of macromers. In some embodiments, thermoplastic polymers could be incorporated. For example, scaffolds based on PCL-DA macromer with poly(L-lactide) (PLLA) polymer can be used to form a semi-interpenetrating polymer network (semi-IPN) compositions version of the SMP with unique properties. The semi-IPN uniquely allows for requisite crystallization of both PCL and PLLA. PCL-PLLA semi-IPNs are able to achieve tunable mechanical properties and accelerated rates of biodegradation, accompanied by surface erosion.

Macromers may be selected according to desired shape memory properties and mechanical properties. Properties may include, but are not limited to, transition temperature, elasticity, biocompatibility, and biodegradability.

SMP macromers may be selected according to their shape memory and mechanical properties. Shape memory macromers may be selected as "soft segments" for use as switching segments in the SMP. The switching segments enable fixation of the temporary shape of the SMP. Other shape memory macromers may be selected as "hard segments" for use as permanent segments in the SMP. The hard segments may determine the crosslink of the SMP foam and enable the permanent shape of the SMP foam. Shape memory macromers that may be used include, but are not limited to, polycaprolactone (PCL), polycaprolactone diacrylate (PCL-DA), polyethylene oxide, polybutadiene, polytetrahydrofuran, polyethylene adipate, polyproylene oxide, polybutylene adipate, poly(vinyl acetate), poly(ethylene terephthalate), methylenebis(4-phenylisocyanate), 1,4-butanediol, polyethylene, and poly(2-methyl-2-oxazoline).

Other macromers may be integrated into the SMP as copolymers for additional or enhanced properties, such as biodegradability, biostability, and porosity. Biodegradable segments include, but are not limited to, polylactide, polyglycolide, polydioxanone, poly(propylene fumerate), and poly(hydroxybutyrate). Biostable segments include, but are not limited to, alkanes, ethers, esters, amides, urethanes, and ureas. The molecular weight of the shape memory macromers may be selected according to desired pore size, degradation, mechanical properties, and transition temperature of the SMP.

The SMP macromers may be physically or chemically crosslinked to form polymer networks. SMP macromers may be chemically crosslinked to form thermosets. For example, a photoinitiator solution may be added to a PCL macromer solution during synthesis and cured with UV light to form a PCL photocrosslinked network. Chemical crosslinking mechanisms include, but are not limited to, covalent bonding and photocrosslinking. SMP macromers may also be physically crosslinked to form thermoplastics. Physical crosslinking mechanisms include, but are not limited to, entanglement and hydrogen bonding. Crosslinks may also be formed by crosslinkers specifically integrated into the SMP for crosslinking.

According to embodiments of the disclosure, the SMP scaffold may be formed by a modified solvent casting/particulate leaching (SCPL) method. Fabrication variables that may be varied or tuned include, but are not limited to, salt particle size, degree of salt fusion, and macromer concentration.

Figure 1:
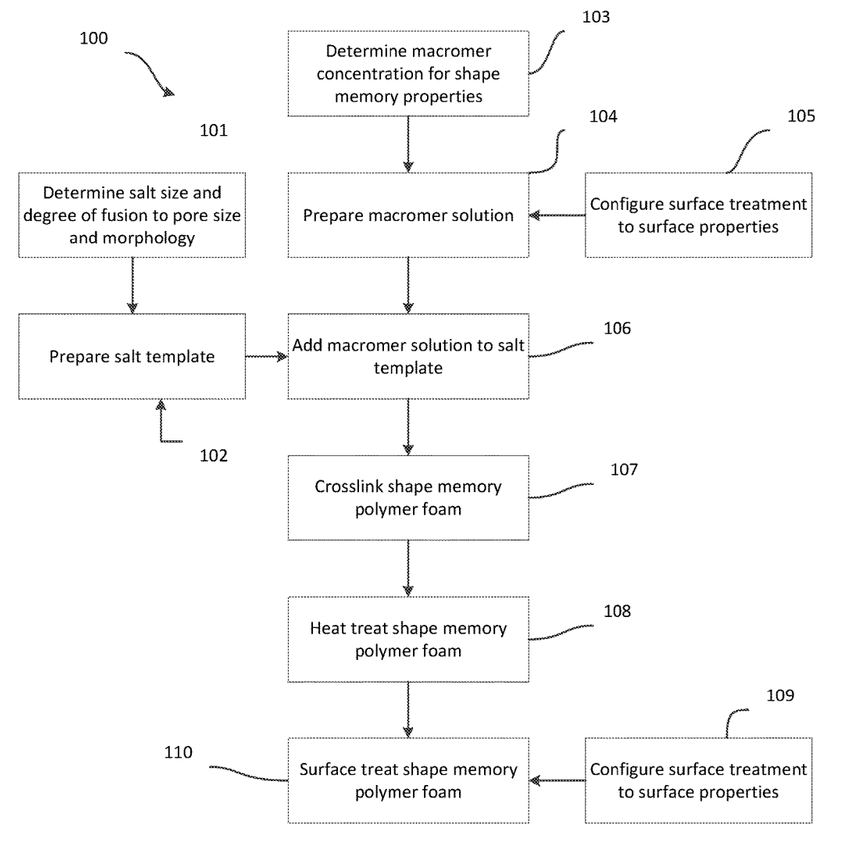
FIG. 1 is an exemplary flow chart of a SMP scaffold fabrication process, according to embodiments of the disclosure.

FIG. 1 is an exemplary flow chart of a SMP scaffold fabrication process 100, according to embodiments of the disclosure. A salt size and degree of fusion may be selected according to desired pore size and pore morphology, as in 101, and a salt template may be prepared, as in 102. A macromer concentration of a macromer solution may be selected and configured according to shape memory properties of the resultant SMP foam, as in 103, and the macromer solution may be prepared, as in 104. A filler may also be determined according to desired mechanical properties, as in 105, and added to the macromer solution. The macromer solution may be added to the salt template, as in 106, and centrifuged. The macromer solution may be crosslinked or polymerized, as in 107, to form the SMP foam. The salt may be leached out and the SMP foam heat treated, as in 108. A surface treatment, such as a coating, may also be configured according to desired surface properties, as in 109, and the SMP foam may be surface treated, as in 110.

The SMP scaffold may include one or more fillers to form a composite scaffold. Fillers may reinforce the SMP scaffold and provide the scaffold with additional or improved mechanical, chemical, and biological properties such as mechanical strength, shape recovery stress, bioactivity, and elastic modulus. For example, surface-functionalized carbon nanotubes may be added to the SMP during the synthesis process to increase the stiffness and shape recovery stress of the resulting composite scaffold. Fillers may be selected according to the desired properties of the SMP scaffold. Fillers that may be used include, but are not limited to, carbon nanotubes, graphene, silicates, phyllosilicates, nanoclays, fibers, biodegradable polymers, glass, and glass ceramics.

The SMP scaffold may include biological treatments for fillers or treatments. Biological treatments may include, but are not limited to, cells, proteins, tissues, blood, serum, healing agents, coagulants, drugs, and therapeutics. These biological treatments may be selected based on the application site of the scaffold and its surrounding tissues. These biological treatments may be added to the scaffold before or after application. These biological treatments may be embedded within the bulk or coated on the surface. Further embodiments may include treatments further supplemented with stem cells, platelets, platelet rich plasma, and serum. Other examples may include bone morphogenic protein, growth factors, and anti-inflammatory agents.

SMP scaffolds may be surface modified with coatings and surface treatments. Coatings may be deposited onto the SMP scaffolds to add or modify properties such as hydrophobicity, hydrophilicity, adhesion, bioactivity, and permeability. Coatings that may be used include, but are not limited to, polydopamine, natural polymers such as collagen, synthetic polymers, glass, ceramic, coupling agents such as silanes, adhesive agents, hydrophilic functional groups, and hydrophobic functional groups. Surface treatments may be applied to the surface of the SMP scaffolds to add or modify properties such as hydrophobicity, hydrophilicty, cellular adhesion, bioactivity, and gene expression.

In certain further embodiments, surface treatments, such as polydopamine, may be applied to increase the scaffold's surface hydrophilicity. In various further embodiments surface treated scaffolds may enhance bioactivity and potential to bond to adjacent bone and be further indicated by various changes, such as hydroxyapatite (HAp) mineralization in polydopamine surface treatments. Surface treated scaffolds may also display an enhanced capacity to support osteoblast adhesion, proliferation, and osteogenic gene expression/extracellular matrix (ECM) deposition. In further embodiments, the surface coating is applied before a heat treatment, to maintain a uniform coating upon the surface. In certain embodiments, it could be possible that the various enhancements are due to an abundant amount of amine and hydroxyl functional groups present in the polydopamine coating. In further embodiments, these functional groups may also increase absorbed protein levels via electrostatic or chemical interactions between the coating and serum proteins. In other embodiments, the surface may be modified via plasma treatment.

The SMP scaffold may be formed or molded into a variety of geometries before application. Geometries that may be produced include, but are not limited to, flat sheets, cylinders, rolls, solid modules, and hollow modules. SMP scaffolds may be implemented and applied using a variety of deformation, molding, and setting techniques. The scaffold may be cut, shaved, or burred according to the desired shape of the defect. Multiple scaffolds may be used, such as in a layered or modular fashion. The scaffold may be molded to a defect, heated above the application temperature, applied to the defect, and cooled to below the application temperature to conformally fit in the defect. A scaffold may be removed and reworked with or without reapplication. The setting of the scaffold may be accelerated with cool media, such as water or air. The scaffold may be delivered arthroscopically.

SMP scaffolds may be used for a variety of bone, osteochondral, cartilage, and other defects. Defects that may be especially suited for SMP scaffolds are defects involving irregularly-shaped surfaces, such as cranial, maxillofacial, dental, orthopedic, and spinal bone defects. Cranial and maxillofacial applications may include cranial expansion repair defects, cranial bone flap fixation, cleft palate repair, mandibular defect repair, and rhinoplasty. Dental applications may include dental/jaw autografts and alveolar grafts. Orthopedic applications may include segmental defects, non- or mal-union, angular limb deformation correction, augmentation of healing in osteoporotic bone, improved mechanical stability and ongrowth/ingrowth of total joint prostheses, augmentation of graft fixation for ACL grafts, Achilles' tendon grafts, or other bone-tendon repair techniques, osteochondral replacement, induction of healing of donor sites in osteochondral autograft systems, and autologous cartilage implantation. Spinal applications may include spinal fusion, spinal non-fusion, and bridging vertebral defects. Osteochondral applications may include auto grafts for damaged joints of the hip, shoulders, and knees. Further embodiments may include scaffolds shaped as autografts (cylindrical) to fill pre-filled holes in damaged joints.

Although the present invention has been described in terms of specific embodiments, it is anticipated that alterations and modifications thereof will become apparent to those skilled in the art. Therefore, it is intended that the following claims be interpreted as covering all such alterations and modifications as fall within the true spirit and scope of the invention.

WORKING EXAMPLES

Example 1

Materials used in the following working example included: PCL-diol (Mn≈10,000 g mol⁻¹), triethylamine (Et₃N), acryloylchloride, 4-dimethylaminopyridine, 2,2-dimethoxy-2-phenyl acetophenone (DMP), 1-vinyl-2-pyrrolidinone (NVP), sodium chloride (NaCl), dopamine hydrochloride, sodium bicarbonate, potassium chloride, potassium phosphate dibasic trihydrate, magnesium chloride hexahydrate, calcium chloride, sodium sulfate, trishydroxymethyl aminomethane (Tris), L-ascorbic acid-2-phophate (AsAP) and all solvents were obtained from Sigma-Aldrich; anhydrous magnesium sulfate and Tris buffer (2 mol l⁻¹) were obtained from Fisher; reagent-grade $CH_2Cl_2$ (dichloromethane, DCM) and NMR grade $CDCl_3$ were dried over 4 Å molecular sieves before use; Dulbecco's Modified Eagle's Medium (DMEM); PSA solution (10 U ml⁻¹ penicillin, 10 g l⁻¹ streptomycin, and 25 mg l⁻¹ amphotericin); Orange Cell Tracker and PicoGreen reagent were obtained from Invitrogen; fetal bovine serum (FBS) was obtained from Atlanta Biologicals; quantitative reverse transcription polymerase chain reaction (RT-PCR) primers for human runX2, osteopontin and β-actin were purchased from Origene; and human osteoblasts were obtained from Lonza, and Western Blot reagents and antibodies were purchased from Santa Cruz Biotechnology.

As an initial step, PCL-diacrylate (PCL-DA) was synthesized. PCL diol (Mn≈10,000 g mol⁻¹) was acrylated according to a previously reported protocol. ¹H NMR spectroscopy was used to confirm acrylation of terminal-OH groups and maintenance of the $M_n$ of PCL.

Cylindrical SMP scaffolds were fabricated. To fabricate each cylindrical scaffold, NaCl salt particles (1.8 g, 459±69 µm) were placed inside a 3 ml glass vial (ID=12.9 mm). To achieve salt fusion, deionized (DI) water (7.5 wt. %) was mechanically mixed with the salt particles in the vial, followed by centrifugation at 4,000 rpm for 15 minutes, and was subsequently air dried overnight. A PCL-diacrylate macromer solution (0.15g ml⁻¹ in DCM) was prepared and combined with photoinitiator solution (15 vol. %, 10 wt. %, DMP in NVP). The solution (0.6 mL) was then added to the fused salt, and the vial was centrifuged at 2,500 rpm for 10 minutes to aid the infiltration of macromer solution to the salt template. Next, the vial was exposed to UV light (e.g., 6 mW cm⁻², 365 nm) for 3 minutes. After air-drying overnight, the SMP scaffold cylinder was removed from the vial, and the salt was leached out by soaking in water/ethanol mixture (1:1 vol.:vol.) for 4 days with daily renewed solvent and subsequently air-dried overnight. To coat polydopamine onto the pore walls, the scaffold was submerged in dopamine hydrochloride solution (2 mg ml⁻¹ in 10 mM Tris buffer, pH=8.5), degassed using a syringe and then maintained at 150 rpm for 16 hours. The scaffold was then extensively rinsed with DI water and dried in vacuo for 24 hours. Finally the scaffold was heat treated at 85° C. for 1 hour, followed by cooling to room temperature (RT). Alternatively, the scaffold was similarly coated after heat treatment for the purpose of comparing with the former process. The final dimensions of the cylindrical foam were ~6 mm (diameter)×~4 mm (height).

PCL SMP films were also prepared in an analogous process. The macromer solution (0.15 g ml⁻¹ in DCM) and photoinitiator (15 vol. %) solution were mixed and pipetted into a rectangular silicone mold (45×22×1.8 mm; McMaster-Carr) sandwiched between two glass slides and exposed to UV light for 3 minutes. After one glass slide and the silicone mold were removed, the edges of the solvent-swollen gel were immediately secured to the remaining slide via binder clips and air dried overnight. After soaking in water/ethanol mixture for 24 hours, the film was sequentially dried in vacuo for 4 hours, soaked in dopamine hydrochloride solution for 16 hours, rinsed with DI water, dried in vacuo for 24 hours, and heated treated at 85° C. for 1 hour before finally cooling to RT.

Differential scanning calorimetry (TA Instruments Q100) was used to evaluate the percentage crystallinity of the SMP scaffolds. The specimen (5-10 mg) was sealed in a hermetic pan, which was then subjected to heating from −30 to 90° C. at 5° C. min⁻¹ under $N_2$. The endothermic melting peak was used to determine the $T_m$ (i.e. $T_{trans}$) and enthalpy change ($\Delta H_m$) of PCL crystalline domains (i.e., switching segments). The following equation was used to determine percentage crystallinity:

$$\% \text{ Crystallinity} = \frac{\Delta H_m}{\Delta H_m^0} \times 100 \qquad \text{Equation (1)}$$

Where $H_m^0$ is 139.5 J g⁻¹ for 100% crystalline PCL. The reported results were an average of three measurements.

The following equation was used to determine percentage porosity (% P) of SMP scaffold:

$$P(\%) = \frac{\rho_{solid\ SMP} - \rho_{solid\ SMP}}{\rho_{solid\ SMP}} \times 100 \qquad \text{Equation (2)}$$

The density (ρ) of the non-porous, bulk PCL SMP ($\rho_{solid\ SMP}$) was gravimetrically determined as 1.119 g cm⁻³. The reported % P results are an average of three measurements.

Scanning electron microscopy (SEM) was used to evaluate the pore interconnectivity of the SMP scaffold. The scaffolds were sequentially freeze-fractured in liquid $N_2$, and the cross sections sputter coated with Au—Pt (~4 nm). SEM images were obtained with an FEI Quanta 600 SEM at an accelerating voltage of 10 kV.

The compressive modulus (E) of cylindrical scaffold at RT ($<T_{trans}$) was measured using an Instron 3345 tensile tester. The specimens was subjected to a constant strain rate of 50% min⁻¹, for both analyses, E values were determined from the initial (3%) linear portion of the resulting stress-strain curves. The reported E values are an average of three measurements.

Shape fixity ($R_f$) and shape recovery ($R_r$) were determined via strain-controlled cyclic-thermal mechanical compression tests performed over two cycles (N) (TA instruments Q800 DMA). For the first shape memory cycle, the cylindrical scaffold was equilibrated at 60° C. ($T_{high}$) for 5 minutes, and compressed to a maximum strain ($\epsilon_m$=50%) at a rate of 50% min⁻¹. It was then held at $\epsilon_m$ for 5 minutes and then cooled to 25° C. ($T_{low}$) to fix the temporary shape. After removing the load and immediately measuring $\epsilon_u$, it was reheated to 60° C. and then compressed to 50% of the height recovered after the first cycle, $R_f$ and $R_r$ for the first (N=1) and second (N=2) cycles were calculated using the following equations:

$$R_f(N) = \frac{\varepsilon_u(N)}{\varepsilon_m} \quad \text{Equation (3)}$$

$$R_r(N) = \frac{\varepsilon_m - \varepsilon_p(N)}{\varepsilon_m - \varepsilon_p(N-1)} \quad \text{Equation (4)}$$

where $\varepsilon_u(N)$ is the ultimate strain the stress-free state in the shape fixation process, $\varepsilon_m$ is 50% $\varepsilon_p(N-1)$ and $\varepsilon_p(N)$ are the final strains of the specimen in the two successive cycles in the stress-free state in the shape recovery process. For N=1, $\varepsilon_p(0)$ equals "zero". The reported $R_f$ and $R_r$ values were an average of three measurements.

The surface wettability of the SMP scaffolds was assessed using a CAM 200 (KSV Instruments) contact angle measurement system equipped with an autodispenser and video camera. A sessile DI water droplet (5 µl) was placed on the cross section of the cylindrical scaffold, and images of the droplet spreading/infiltration over 2 minutes were recorded.

SMP scaffold was cut in half with a clean blade, and one half was individually placed into a sealed centrifuge tube containing 30 ml of 1× SBF maintained at 37° C. At 7 days and 14 days, the scaffold specimens were retrieved, air dried (24 hours, RT) and HAp formation visualized by imaging with SEM (FEI Quanta 600 SEM). To confirm the composition of HAp, powder X-ray diffraction (XRD) data were collected on a Bruker D8 diffractometer fitted with Lynx-EYE detector (Cu Kα; 40 kV, 40 mA; Bragg-Brentano geometry; scan range, 5-70°; step size, 0.05°; step time, 1 second).

Cell Culture and SMP Sterilization was performed: cryopreserved human osteoblasts were thawed and expanded in monolayer culture between passages 3 and 5. Cells were maintained at 37° C. in DMEM (5% $CO_2$), supplemented with FBS (10%), AsAP (50 µg ml$^{-1}$) and PSA (1%). Polydopamine-coated and uncoated SMP solid films (thickness≈0.8 mm, n=6 per formulation) and porous scaffolds (height≈3 mm, n=5 per formulation) were punched into 6-mm diameter discs. These discs were sterilized by exposure to ethylene oxide (Andersen Sterilizers Inc.).

The cytotoxicities of polydopamine-coated and uncoated SMP solid films (n=3 per formulation) were evaluated relative to a tissue culture polystyrene control using indirect assessment. Films were placed in a 12-well-plate tissue culture plate and transwell inserts (Falcon, 0.8 µm pores) were placed over each film as well as into three empty control wells. Human osteoblasts were then seeded into the insert at 5,000 cells cm$^{-2}$. Each well was filled with 1 ml of DMEM supplemented with FBS (10%), AsAP (50 µg ml$^{-1}$) and PSA (1%) and cultured at 37° C. in 5% $CO_2$. After 24 hours, media were collected from each insert, and levels of cell death were evaluated by measuring lactate dehydrogenase (LDH) levels (LDH Cytotoxicity kit; Roche).

Polydopamine-coated and uncoated SMP solid films (n=3 per formulation) were placed in a 24-well plate and held in place by a cylindrical Teflon weight (0.9 cm inner diameter). Human osteoblasts previously labeled with orange cell tracker were seeded onto the films at 2,000 cells cm$^{-2}$. Seeded films were cultured at 37° C. in DMEM (5% $CO_2$) supplemented with FBS (10%), AsAP (50 µg ml$^{-1}$), and PSA (1%) for 24 hours. Films were fixed with formalin overnight at 4° C. Adherent cells were imaged under fluorescence from at least three regions of each film using a Zeiss Axiovert 200 M microscope. For each image, the average cell area (spreading) was quantified by applying the Photoshop (version 9.0) "magic wand" tool to the image background and adjusting the tool tolerance so that all extracellular regions were selected. The histogram function was then used to evaluate the number of extracellular pixels. The average number of pixels per cell ($A_{cell}$) for that image was then quantified as follows:

$$A_{cell}=\text{(total image pixels-extracellular pixels)/(total cell number in image).} \quad \text{Equation(5)}$$

This pixel-based area value was converted to square microns using the known image scaling.

Polydopamine-coated and uncoated SMP scaffolds (n=5 per formulation, diameter 6 mm and height 3 mm) were placed into a 12-well-plate tissue culture plate. Human osteoblasts were harvested and resuspended in DMEM supplemented with FBS (10%), AsAP (50 µg ml$^{-1}$), and PSA (1%) in order to reach a cell density of 4×10$^6$ cells ml$^{-1}$. The cell suspension (50 µl) was pipetted onto the upper surface of each scaffold and incubated for 15 minutes. Next, the cell suspension (50 µl) was similarly seeded onto the opposite surface of each scaffold and incubated for 15 minutes. This seeding process was then repeated. Following cell seeding, cells not attached to scaffolds surfaces were removed by rinsing the scaffolds three times with PBS. Scaffolds were then transferred to a new well plate and were cultured in DMEM (supplemented with 10% FBS, 50 µg ml$^{-1}$ AsAP and 1% PSA) for 72 hours at 5% $CO_2$.

Scaffolds harvested at 72 hours were transferred to Rnase-free microfuge tubes, flash frozen in liquid nitrogen and stored at −80° C. until time of analysis. PolyA-mRNA was subsequently isolated from each scaffold using a Dynabeads mRNA Direct kit (Invitrogen). In brief, each scaffold was immersed in kit cell lysis buffer and PolyA-mRNA was isolated from each lysis solution using Oligo-(dT) magnetic beads. The remaining solution was analyzed for DNA levels as a measure of cell number as well as for protein expression by Western Blot. DNA was assessed using the PicoGreen kit (Invitrogen) and converted to cell number using the conversion factor of 6.6 pg DNA per cell.

RT-PCR was conducted using the Superscript III Platinum SybrGreen One Step qRT-PCT kit and the Step One Real-Time PCR System (Applied Biosystems). mRNA levels for each gene of interest were assessed in duplicate for each scaffold. Template (7 µl) and 1 µM primer (0.5 µl) were added per 25 µl of reaction mixture. Amplification during the PCR phase was monitored by measuring the change in SybrGreen fluorescence. A threshold fluorescence value at which each sample was in the exponential phase of amplification was identified using Step One Software v2.0 (Applied Biosystems). The amplification cycle at which a given sample crossed this threshold was recorded as the $C_t$ for that sample. RunX2 and osteopontin gene expression levels were then calculated relative to β-actin using the $\Delta\Delta C_t$ method, with osteoblast gene expression prior to scaffold seeding (referred to as "day 0" expression) used as a reference.

For Western Blot analyses, sample homogenate volumes representing 150 ng of DNA were loaded into separate wells of 10% SDS-PAGE gel. Following protein separation and transfer onto a nitrocellulose membrane, the blots were then blocked with a 5% BSA solution in Tris-buffered saline containing 0.1% Tween-20 (TBST; 25 mM Tris-HCL, pH. 7.5, 137 mM NaCl, 0.1% Tween 20) for 1 hour at room temperature. Each blot was incubated with the osteopontin primary antibody (clone AKm2A1) diluted TBST solution containing 5% BSA overnight at 4° C., after which alkaline phosphatase (AP)-conjugated secondary antibody (Jackson Immunoresearch) was applied for 1 hour at room temperature. Signal was detected using an AP chemiluminescent solution (Novex). Imaging was performed using the Molecular Imager Chemidoc XRS system (Biorad), and the band optical density was quantified using Adobe Photoshop. All cell culture results were given as mean±standard deviation. Sample means were compared using ANOVA followed by Tukey's post-hoc test (P<0.05).

PCL SMP scaffolds were produced via a revised SCPL protocol using the following parameters: salt size (459±69 µm), salt fusion (7.5 wt. % water added to salt) and photocrosslinkable PCL-DA macromer ($M_n \approx 10,000$ g mol$^{-1}$) concentration in DCM (0.15 g ml$^{-1}$). Following salt leaching and drying, the SMP foams were heat treated at 85° C. (T>$T_m$), which induced foam densification (i.e., shrinking). It was previously noted that heat treatment was essential to shape memory behavior, and hypothesized to be due to PCL crystalline domains reorganizing into closer proximity. In order to determine the optimal fabrication state at which to apply the polydopamine coating, the coating efficiency of applying immediately before and immediately after heat treatment was compared. Herein, the observed uniformity of the characteristic brown color of the resulting polydopamine coating throughout the scaffold was used to qualitatively assess coating efficiency. When the coating was applied to the SMP scaffold after heat treatment (i.e., after densification), scaffold cross sections exhibited non-uniform color appearance, indicating irregular coverage. In contrast, when applied before heat treatment (i.e., before densification), the visually observed consistent coloration throughout the scaffold indicated a macroscopically uniform polydopamide coating. Subsequent heat treatment of the polydopamine-coated scaffold caused the color to darken, owing to scaffold densification or thermal oxidation. The observed differences in polydopamine coating distribution when applied immediately after vs. immediately before heat treatment can be explained by the differences in pore size and percentage porosity before vs after heat treatment. While the pores remained interconnected, heat treatment caused a reduction in pore size and percentage porosity (% P). Thus, prior to heat treatment, diffusion of the dopamine solution throughout the scaffold was enhanced. Compared with their uncoated counterparts, the scaffolds after coating with polydopamine and following heat treatment, displayed similar pore size and % P. In addition, higher magnification revealed characteristic polydopamine nanoparticles within the coating.

Finally, $T_m$ and percentage crystallinity as well as compressive modulus (E) were compared for PCL SMP scaffolds with or without the polydopamine coating. For both non-heat-treated and heat-treated samples, application of a polydopamine coating did not significantly change the values of these parameters. $T_m$ and percentage crystallinity decreased slightly after heat treatment because of higher PCL chain mobility and hence the ability to form crystalline domains from solution (i.e., during photocrosslinking) vs. from the bulk (i.e. during sequential heating and cooling). Due to scaffold densification, heat treated scaffolds exhibited a substantial increase in E at RT from ~0.54 MPa to ~4.3 MPa. The E values of heat-treated scaffolds are comparable to those of other scaffolds studied for bone regeneration and higher than that of conventional polyurethane porous SMP (~1 MPa). Given these results, coated SMP scaffolds for subsequent analyses were prepared by applying the polydopamine coating immediately before heat treatment. In the case of PCL SMP solid films, the polydopamine coating was similarly applied before heat treatment.

The self-fitting nature of the PCL-based SMP scaffold hinges on its temperature-dependent mechanical and shape memory properties. First, in order to conformably self-fit into an irregular defect, the scaffold must exhibit a substantial reduction in E when heated above $T_{trans}$ ($T_m \approx 56°$ C.). For the polydopamine-coated scaffold, E was reduced from 4.4 MPa to ~12 kPa after heating to 60° C. This large reduction in E is attributed to the melting of the PCL crystalline domains. As a result, the scaffold softened and became malleable such that it could be pressed by hand into a model defect. With the release of manual pressure, the scaffold expanded because of shape recovery, which led to "fitting" as the scaffold filled irregular boundaries of the defect. Upon cooling, the PCL crystalline domains reformed, locking the scaffold into the new temporary shape. The temporary shape was retained even after removing the scaffold from the defect. Subsequent SEM analysis of this removed scaffold revealed that most pores remained quite open along the edges (i.e. areas in previous contact with the mold). Key parameters in quantifying a scaffold's shape memory, and, hence, self-fitting behavior are the shape recovery ($R_r$) and shape fixity ($R_f$) properties. $R_r$ and $R_f$ describe the scaffold's expansion within the defect (T>$T_{trans}$), and subsequent fixation of the new temporary shape (T<$T_{trans}$), respectively. Thus, these parameters were measured for two cycles for the polydopamine-coated scaffold. $R_r$ was ~95% for the first shape memory cycle (N=1) and increased to ~100% for the second cycle (N=2). An increase in $R_r$ was noted previously for both solid and porous SMP as well as $R_f$ values>100%, including in previous reports on PCL-based SMP. Thus coated scaffolds' ability to be fitted within the defect for two heating cycles was confirmed.

Polydopamine coatings have been characterized as being rich in amine and hydroxyl functional groups. Thus, they have been used to increase the hydrophilicity of hydrophobic polymers. The enhanced hydrophilicty of polydopamine-coated PCL SMP scaffolds was determined by examining the spreading of an applied water droplet as a function of time vs that of an uncoated control. For the coated scaffold, the water droplet quickly spread and was absorbed within ~120 seconds, whereas the insignificant spreading occurred for the uncoated scaffold. In addition to enhanced hydrophilicity, the negatively charged functional groups of polydopamine coatings induce apatite mineralization when exposed to simulated body fluid (SBF). After soaking in SBF (1×), the extent of formation of HAp is a qualitative indicator of bioactivity and corresponds to a scaffold's ability to bond to bone in vivo. Thus, polydopamine-coated SMP scaffolds were exposed to SBF, and the mineralization was observed at 7 and 14 days. SEM images revealed that mineralization became increasingly more significant with time. The uncoated SMP scaffold showed no mineralization, even after 14 days. To verify HAp formation, XRD was performed on the mineralized polydopamine-coated SMP scaffold (14 days) and compared with the scaffold prior to mineralization (0 days) as well as an uncoated control (14 days). For the former, a characteristic of HAp diffraction peak around 2θ=32° indicative of reflections from (2 1 1) and (3 0 0) plans was observed, compared with the high peaks for PCL crystalline domains at 2θ=21.5° and 2θ=23.9°. HAp exhibited a low and broad peak because of the low degree of crystallinity associated with bone-like apatite formed in SBF solution.

Cytocompatibility of the SMP surfaces was confirmed by assessing the LDH levels released by human osteoblasts following exposure for 24 hours to uncoated and polydopamine-coated SMP films. LDH is a soluble cytosolic enzyme that is released into the culture medium following damage of the plasma membrane as a result of apoptosis or necrosis. The cytotoxicity of uncoated and polydopamine-coated SMP surfaces could not be statistically distinguished from tissue culture polystyrene controls, as anticipated (P=0.11).

To examine the ability of the SMP scaffolds to support sustained osteoblast adhesion and proliferation, osteoblasts were seeded and cultured on the surfaces of uncoated and polydopamine-coated SMP scaffolds. Seeding resulted in even cell distribution throughout the scaffold. After 72 hours of culture, adherent cells were lysed, and the levels of DNA were measured and compared. Polydopamine-coated SMP scaffolds supported cell adhesion and proliferation at levels that were approximately five-fold greater than that of uncoated SMP scaffolds. Consistent with the adhesion results, osteoblasts spread to a significantly greater extent on the surfaces of polydopamine-coated SMP films relative to uncoated SMP films, as determined by cell area measurements. Cell adhesion and spreading are regulated in part by the nature of the serum protein adsorption on the scaffold surface. Similarly, the nature of cell adhesion regulates the capacity of a material to support cell proliferation. In view of this, the present results are consistent with recent studies indicating that polydopamine coatings minimize the denaturation of adsorbed cell-adhesion proteins by adjusting the surface energy of non-wetting polymer surfaces, resulting in improved cell adhesion and proliferation. The enhanced cell adhesion and proliferation might also be attributed to the abundant amine and hydroxyl functional groups present in the polydopamine coating, which may increase adsorbed protein levels via electrostatic or chemical interactions between the coating and serum proteins.

Osteoblasts were cultured on uncoated and polydopamine-coated scaffolds to further elucidate the capacity of SMP scaffolds to support new bone formation. After a period of 72 hours, osteoblast expression of the runX2 and osteopontin (SPP1) was analyzed by RT-PCR. RunX2 is a key osteogenic transcription factor capable of up-regulating the expression of genes associated with new bone formation. Osteopontin is an extracellular matrix (ECM) protein, which plays a critical role in bone function. Osteoblasts cultured on polydopamine-coated scaffolds displayed on a 2-fold and 1.4-fold increase in runX2 and SPP1 gene expression, respectively, relative to the initial (pre-seeding) expression levels. The coated samples displayed a 1.6 fold increase in runX2 gene expression relative to the uncoated samples. Osteoblast expression of runX2 and SPP1 on uncoated scaffolds could not be statistically distinguished from pre-seeding (day 0) levels. Examining osteopontin levels at the protein level, coated scaffolds supported twice the osteopontin deposition of uncoated scaffolds per mg total sample dry weight.

A polydopamine-coated SMP scaffold was prepared via a revised SCPL method including photocrosslinking of PCL-DA in the presence of a fused NaCl salt template. As a thermoresponsive shape memory material, the scaffold was capable of conformally fitting into an irregular model defect. While malleable at $T > T_{trans}$ ($T_{trans} = T_m$ of PCL), cooling locked the scaffold into its new temporary shape. The scaffold displayed highly interconnected pores and a modulus (4.4 MPa) comparable to other scaffolds used to support bone growth. The polydopamine coating did not affect the pore features, thermal, mechanical, and the shape memory properties of the SMP scaffold. After soaking in SBF for 7 and 14 days, polydopamine-coated scaffolds showed significant HAp mineralization, indicating their bioactivity and potential to bond to adjacent bone. Polydopamine-coated scaffolds also displayed an enhanced capacity to support osteoblast adhesion, proliferation, and osteogenic gene expression/ECM deposition. Thus, it is anticipated that this porous, PCL SMP foam could be useful as a self-fitting scaffold to treat CMF bone defects, given its ability to be positioned within a defect and its osteoconductive and bioactive characteristics.

Example 2

PCL-based SMPs have been modified with copolymer segments, including polyurethanes, poly(ethylene glycol) and poly(n-butyl acrylate). However, poly(L-lactic acid) (PLLA) represents a potentially useful option due to its biodegradability as well as high modulus (E~2.7 GPa), which stems from its semi-crystallinity and relatively high $T_g$ (~60° C.). While SMPs comprised of PCL and PLLA have been reported, they have often been formed as copolymers, including random copolymers (such that the $T_{trans}$ is the PLLA $T_g$ rather than the PCL $T_m$) or as cross-linked PCL-PLLA copolymer single networks. In contrast, we report herein PCL-PLLA SMPs formed as semi-interpenetrating networks (semi-IPNs) based on the combination of a PCL-DA network with thermoplastic PLLA. Importantly, since cross-linking is known to reduce chain mobility, and hence crystallization, incorporation of non-crosslinked PLLA into the PCL network was expected to yield the desired PLLA semi-crystallinity and broadening of mechanical properties as well as degradation rates.

Herein, PCL-PLLA SMP semi-IPNs were prepared with varying PCL:PLLA weight % ratios (100:0 [PCL-DA control], 90:10, 75:25, 60:40) and with varied PCL-DA molecular weight (n=30, 45). Following UV cross-linking, the effects on shape memory behavior, thermal properties (i.e. crystallinity and Tm), mechanical properties (i.e. stiffness and strength) and degradation rate were studied.

Materials used in the following working example included: Poly(ε-caprolactone) diol ($PCL_{90}$-diol; $M_n$~10,000 g/mol), ε-caprolactone, l-lactide, stannous 2-ethylhexanoate, triethylamine ($Et_3N$), acryloyl chloride, 4-dimethylaminopyridine (DMAP), 2,2-dimethoxy-2-phenylacetophenone (DMP), 1-vinyl-2-pyrrolidinone (NVP), potassium carbonate ($K_2CO_3$), sodium hydroxide (NaOH), etheylene glycol and solvents were obtained from Sigma-Aldrich. Anhydrous magnesium sulfate ($Mg_2SO_4$) was obtained from Fisher. Reagent-grade $CH_2Cl$ and NMR-grade $CDCl_3$ were dried over 4 Å molecular sieves prior to use.

$PCL_{2n}$-diol and $PLLA_{2m}$-diol were synthesized by the ring-opening polymerization of ε-caprolactone or l-lactide, respectively, in the presence of ethylene glycol initiator and stannous 2-ethylhexanoate catalyst. The degree of polymerization (n, m) was controlled by the ratio of monomer to ethylene glycol. The resulting terminal hydroxyl groups of $PCL_{2n}$-diol were subsequently converted to photosensitive acrylate (OAc) groups by reacting with acryloyl chloride. The number average molecular weights ($M_n$) were determined by $^1H$ NMR.

Solutions (25 wt % $CH_2Cl_2$) of PCL:PLLA (100:0 [PCL-DA control], 90:10, 75:25, 60:40 wt % ratio) were prepared with 15 vol % of a photoinitator solution (10 wt % DMP in NVP). The solution was transferred to a circular silicone mold (45 mm×2 mm; McMaster-Carr) secured between glass slides and exposed to UV light (UV-Transilluminator, 6 mW cm-2, 365 nm) for 3 minutes per side. The solvent-swollen disc was sequentially removed from the mold, air dried (RT, 12 hours), dried in vacuo (36 in·Hg, RT, 4 h), soaked in ethanol (3 hours) and air dried. The disc was finally annealed (36 in·Hg, 85° C., 1 hour) and allowed to set at RT (48 hours) before testing.

Discs (~8 mm×~1.1 mm; N=3) were immersed in 10 mL $CH_2Cl_2$ and maintained for 48 hours at 150 rpm. Swollen discs were then removed, air dried and dried in vacuo (36 in·Hg, RT, ~24 hours), and the mass of dried discs was determined to quantify percent mass loss (i.e. sol content).

Differential scanning calorimetry (DSC, TA Instruments Q100) of specimens (~12 mg; N=3) in hermetic pans was ran from RT to 200° C. at a heating rate of 5° C. min$^{-1}$. From the endothermic PCL and PLLA melting peaks and enthalpy change (ΔHm) were measured. Percent crystallinity (% $\chi_c$) was calculated via Equation (6):

$$\%\chi_c = \frac{\Delta H_m}{\Delta H_m^0} \times 100 \qquad \text{Equation (6)}$$

where $\Delta H_m$ was calculated by the area of the melting peak, and $\Delta H°_m$ is the enthalpy of fusion of 100% crystalline PCL (139.5 J g$^{-1}$) or PLLA (93.0 J g$^{-1}$).

Rectangular specimens (~20 mm×~3.3 mm×~1.1 mm) were subjected to the following sequence: (1) after exposure to a water bath at 80° C. ($T_{high}$) for 1 minute, deform the film strip into a coiled shape with a metal mandrel, (2) place the film in an ice bath (~0° C., $T_{low}$) for 1 minute to fix this temporary shape, (3) place the fixed coil in the 80° C. water bath and observe recovery at t=0 and 8 seconds.

Tensile properties were evaluated at RT with a tensile tester (Instron 3340) by subjecting rectangular strips (~15 mm×~3.3 mm×~1.1 mm; N=5-10) with a gauge length of ~3 mm to a constant strain rate (50 mm min$^{-1}$) in tension until break. From the resulting stress-strain curves, modulus (E), tensile strength (TS) and strain at break (% ε) were determined.

Discs (~7 mm×~1.1 mm; N=3) were immersed in 20 mL of 1M NaOH in a centrifuge tube maintained at 37° C. via a water bath. Every 8 hours for 72 hours, the samples were taken from solution, thoroughly rinsed with DI water, blotted and dried in vacuo (36 in·Hg, RT, ~16 hours). The mass and thickness of the samples were determined prior to returning to fresh NaOH solution. At 48 hours, a sample was imaged via scanning electron microscopy (SEM). Surfaces and cross sections were subjected to Au—Pt coating (~4 nm). Images were obtained using a JEOL 6400 SEM with an accelerating voltage of 10 kV.

Data was reported as the mean±standard deviation. Values were compared using a Student's t-Test to determine p-values.

Sol content of PCL-PLLA semi-IPNs was determined to confirm that PCL-DA underwent a high degree of cross-linking in the presence of PLLA. For the PCL-DA network controls, sol content was ~8%. For semi-IPNs, sol content did not deviate from, approximately, the combined value of the sol content observed for controls and the amount of PLLA, which was extractable due to its non-crosslinked nature.

$T_m$ and % crystallinity for both PCL and PLLA components were determined for all networks, as set forth in Table 1 below:

As observed previously, the PCL-DA control networks exhibited the crystallinity required to serve as shape memory switching segments. Crystallinity was higher for networks prepared with PCL-DA n=45 versus n=30, with longer PCL chains between cross-links more able to organize into lamellae. PCL-PLLA semi-IPNs permitted PCL crystallization, although this decreased somewhat with increased PLLA content. We attribute diminished crystallinity to the reduction of PCL chain mobility and overall decreased proximity among PCL chains when surrounded by an increasing concentration of thermoplastic PLLA chains. In addition, as molecularly-mobile un-crosslinked chains within the PCL-DA network, PLLA also exhibited the ability to crystallize, with crystallinity increasing with PLLA content.

Upon placement in 80° C. ($T_{high}$) water, the extent of shape recovery from the "fixed," temporary shape (coil) to the permanent shape (flat strip) was observed. By 8 seconds, versus the PCL-DA network controls, PCL-PLLA semi-IPNs had not quite achieved the full recovery seen for PCL-DA controls. Continued exposure at 80° C. did not yield complete recovery. As the switching segment for shape memory behavior, PCL crystalline domains maintain the temporary shape and, upon melting, dictate recovery. For the semi-IPNs at 80° C., although the PCL-DA network is in the melted state (T>$T_m$), PLLA remains semi-crystalline ($T_m$~175° C.). Thus, we hypothesize that semi-crystalline PLLA regions slightly limit full recovery by restricting PCL chain mobility and the associated switching segment effect.

The tensile modulus (E), tensile strength (TS) and strain at break (% ε) were determined for all SMP networks (e.g. see Table 1). For PCL-PLLA semi-IPNs, when the PLLA content was increased to 75:25 wt % (PCL:PLLA), an increase in E was observed versus the corresponding PCL-DA network controls. A continued increase in PLLA content (60:40 wt % [PCL:PLLA]) yielded reduced E values, with the n=30 semi-IPN fracturing when secured in clamps. This brittle behavior is attributed to a high total crystallinity, from both PCL and PLLA components. Due to an increased cross-link density, E was higher for the 75:25 wt % (PCL:PLLA) prepared with n=30 versus n=45 PCL-DA. In the case of TS, values of PCL-DA network controls and PCL-PLLA semi-IPNs were higher when prepared with n=45 rather than n=30 PCL-DA. Due to a reduced cross-link

TABLE 1

Thermal and mechanical properties of SMP networks

| PCL:PLLA Ratio | PCL, n | PCL $T_m$ [° C.] | Cryst. [%] | PLLA $T_m$ [° C.] | Cryst. [%] | Tensile Modulus, E [MPa] | Tensile Strength, TS [MPa] | Strain at Break, ε [%] |
|---|---|---|---|---|---|---|---|---|
| PCL-DA Control | 30 | 48.8 ± 0.3 | 34.6 ± 1.1 | N/A | N/A | 75.8 ± 7.7 | 18.4 ± 1.9 | 707 ± 150 |
| 90:10 | 30 | 49.2 ± 0.3 | 30.9 ± 2.2 | 146.0 ± 0.8 | 5.4 ± 1.2 | 83.9 ± 11.6 | 19.0 ± 2.2 | 752 ± 140 |
| 75:25 | 30 | 49.1 ± 0.5 | 25.4 ± 1.5 | 157.9 ± 0.7 | 15.4 ± 0.9 | 93.3 ± 9.3 | 18.8 ± 1.1 | 593 ± 190 |
| 60:40 | 30 | 49.7 ± 0.3 | 21.2 ± 0.5 | 157.6 ± 0.6 | 28.9 ± 0.6 | N/A$^{a)}$ | N/A$^{a)}$ | N/A$^{a)}$ |
| PCL-DA Control | 45 | 54.5 ± 0.2 | 43.5 ± 0.4 | N/A | N/A | 67.3 ± 6.4 | 23.4 ± 2.1 | 1350 ± 99 |
| 90:10 | 45 | 53.2 ± 0.3 | 39.8 ± 1.7 | 146.7 ± 0.5 | 5.3 ± 1.6 | 71.9 ± 9.8 | 24.5 ± 0.9 | 1350 ± 240 |
| 75:25 | 45 | 52.8 ± 0.1 | 31.0 ± 0.3 | 152.7 ± 0.3 | 16.7 ± 0.5 | 77.3 ± 4.7 | 23.4 ± 1.9 | 1230 ± 160 |
| 60:40 | 45 | 52.7 ± 0.3 | 26.0 ± 0.8 | 152.7 ± 0.3 | 25.8 ± 0.6 | 63.07 ± 8.3 | 16.5 ± 1.2 | 167 ± 200 | density, these networks were able to undergo more strain, permitting them to reach a higher maximum stress. Semi-IPNs based on 90:10 and 75:25 wt % PCL:PLLA exhibited statistically similar TS values versus the corresponding PCL-DA network control.

Degradation behavior was assessed under accelerated conditions (1M NaOH, 37° C.) in terms of mass loss as well as the observed physical erosion. Weight loss occurred at an unexpected, substantially higher rate for PCL-PLLA semi-IPNs versus the corresponding PCL-DA network controls, which showed effectively negligible weight loss. For semi-IPNs based on PCL-DA n=30, an increased PLLA content produced a systematic increase in weight loss. For those based on PCL-DA n=45, differences in weight loss with PLLA content were less pronounced, perhaps due to the relatively lower cross-link density that enhanced degradation overall. Interesting erosion behavior accompanied the degradation of semi-IPNs. While PCL and PLLA are known to degrade through bulk erosion, surface erosion was observed to occur for the semi-IPNs such that specimen thickness decreased over time. We hypothesize that initially, the rate of degradation of un-crosslinked PLLA surpassed that of cross-linked PCL. Thus, PLLA degradation products were removed more quickly from the surface via a shorter diffusion pathway. This resulted in a lower density at the surface relative to the bulk, which is known to localize erosion to the surface. We confirmed that this behavior was not due to the dissolution and extraction of PLLA, as samples under non-accelerated conditions (pH~7, 37° C.) did not show detectable mass loss from a 60:40 wt % (PCL:PLLA) semi-IPN.

In this work, PCL-PLLA SMP semi-IPNs were prepared via the photochemical cure of PCL-DA and PLLA. The PCL:PLLA weight % ratios were varied (100:0 [PCL-DA control], 90:10, 75:25, 60:40) as was the PCL-DA molecular weight (n=30, 45). The PCL-DA network provided the switching segments (i.e., $T_m=T_{trans}$) and netpoints (i.e. chemical cross-links) required for shape memory behavior, while un-crosslinked PLLA was incorporated to broaden and tailor properties. Due to semi-IPN design, PCL underwent sufficient crystallization (21-40% crystallinity) for shape memory, while PLLA also exhibited the desired semi-crystallinity. Whereas 75:25 wt % (PCL:PLLA) semi-IPNs exhibited an increased E (n=30: ~93 MPa; n=45: ~77 MPa) over corresponding PCL-DA network controls (n=30: ~76 MPa; n=45: ~67 MPa), TS was higher for controls and semi-IPNs prepared with n=45 PCL-DA (~23-25 MPa) rather than n=30 (~18-19 MPa). Under accelerated conditions, while PCL-DA network controls exhibited minimal degradation (~5% loss) after 72 hours (1M NaOH, 37° C.), PCL-PLLA semi-IPNs degraded rapidly (~80-100% loss) and also exhibited surface erosion. With their broadened properties, these semi-IPNs may enhance the utility of biodegradable SMPs.

Conditional language used herein such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. A method of making a shape memory polymer (SMP) tissue scaffold, the method comprising:
    forming a salt template;
    adding a mixture to the salt template, wherein the mixture comprises a macromer solution and at least one photoinitiator solution;
    forming a SMP scaffold, wherein the SMP scaffold comprises poly(ε-caprolactone) diacrylate macromer with poly(L-lactide) polymer that forms a semi-interpenetrating polymer network within the SMP scaffold;
    drying the SMP scaffold;
    leaching salt from the SMP scaffold;
    applying a coating to the SMP scaffold; and
    drying the SMP scaffold.

2. The method of claim 1, comprising:
    heating, the SMP scaffold after the drying.

3. The method of claim 1, comprising:
    heating, the SMP scaffold after the leaching.

4. The method of claim 1, comprising centrifuging the mixture after adding the mixture to the salt template.

5. The method of claim 1, comprising exposing the SMP scaffold to UV light after adding the mixture to the salt template.

6. The method of claim 1, comprising degassing the SMP scaffold after submersion in coating solution.

7. The method of claim 1, comprising rinsing the SMP scaffold in deionized water after applying the coating to the SMP scaffold.

8. The method of claim 1, wherein forming the SMP scaffold comprises creating a salt template from salt having a salt size and a degree of salt fusion.

9. The method of claim 8, wherein creating a salt template comprises placing salt particles into a container, adding deionized water to the container, and centrifuging the salt template.

10. The method of claim 1, wherein drying the SMP scaffold comprises drying the SMP scaffold in vacuo.

11. The method of claim 1, wherein the macromer solution includes polycaprolactone diacrylate.

12. The method of claim 1, wherein the SMP scaffold comprises a biostable segment that includes an alkane.

13. The method of claim 1, wherein the SMP scaffold comprises a filler that includes glass.

14. The method of claim 1, wherein the SMP scaffold comprises a biological treatment that includes cells.

15. The method of claim 1, wherein the coating includes polydopamine.

* * * * *